US005620486A

United States Patent [19]
Cherpeck

[11] Patent Number: 5,620,486
[45] Date of Patent: Apr. 15, 1997

[54] FUEL COMPOSITIONS CONTAINING ARYL SUCCINIMIDES

[75] Inventor: Richard E. Cherpeck, Cotati, Calif.

[73] Assignee: Chevron Chemical Company, San Ramon, Calif.

[21] Appl. No.: 366,534

[22] Filed: Dec. 30, 1994

[51] Int. Cl.$^6$ ................................................. C10L 1/22
[52] U.S. Cl. ........................ 44/347; 44/348; 548/546; 548/547
[58] Field of Search ................ 44/348, 347, 331, 44/545; 548/546, 547; 508/290, 291, 293

[56] References Cited

U.S. PATENT DOCUMENTS

| | | | |
|---|---|---|---|
| 3,039,860 | 6/1962 | Andress, Jr. et al. | 548/547 |
| 3,147,933 | 9/1964 | Ley et al. | |
| 3,149,933 | 9/1964 | Ley et al. | 44/75 |
| 3,194,812 | 7/1965 | Norman et al. | 44/347 |
| 3,434,814 | 3/1969 | Dubeck et al. | 44/69 |
| 3,756,793 | 9/1973 | Robinson . | |
| 3,849,085 | 11/1974 | Kreuz et al. | 44/78 |
| 4,134,846 | 1/1979 | Machleder et al. | 252/51.5 A |
| 4,191,537 | 3/1980 | Lewis et al. | |
| 4,320,020 | 3/1982 | Lange . | |
| 4,320,021 | 3/1982 | Lange . | |
| 4,347,148 | 8/1982 | Davis | 252/51.5 R |
| 4,354,950 | 10/1982 | Hammond et al. | 252/51.5 A |
| 4,386,939 | 6/1983 | Lange . | |
| 4,820,432 | 4/1989 | Lundberg et al. | 252/51.5 A |
| 4,877,416 | 10/1989 | Campbell . | |
| 5,004,478 | 4/1991 | Vogel . | |
| 5,266,081 | 11/1993 | Avery et al. | 44/347 |

Primary Examiner—Margaret Medley
Attorney, Agent, or Firm—Claude J. Caroli

[57] ABSTRACT

A fuel composition comprising a major amount of hydrocarbons boiling in the gasoline or diesel range and an effective detergent amount of a compound of the formula:

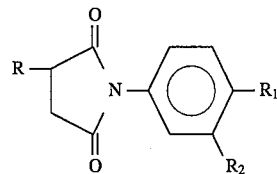

wherein R is a hydrocarbyl group having an average molecular weight of about 400 to 5,000; and $R_1$ and $R_2$ are independently selected from the group consisting of hydrogen, hydroxy, —$CO_2H$, —$NO_2$, and —$NR_3R_4$, wherein $R_3$ and $R_4$ are independently hydrogen or lower alkyl of 1 to 6 carbon atoms; provided that $R_1$ and $R_2$ cannot both be hydrogen.

27 Claims, No Drawings

FUEL COMPOSITIONS CONTAINING ARYL SUCCINIMIDES

BACKGROUND OF THE INVENTION

1. Field of the Invention

This invention relates to fuel compositions containing aryl succinimides. More particularly, this invention relates to the use of aryl succinimides in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels. Similar amino phenols are disclosed in related U.S. Pat. No. 4,320,020, issued Mar. 16, 1982 to R. M. Lange. Similarly, U.S. Pat. No. 3,149,933, issued Sep. 22, 1964 to K. Ley et al., discloses hydrocarbon-substituted amino phenols as stabilizers for liquid fuels.

U.S. Pat. No. 4,386,939, issued Jun. 7, 1983 to R. M. Lange, discloses nitrogen-containing compositions prepared by reacting an amino phenol with at least one 3- or 4-membered ring heterocyclic compound in which the hetero atom is a single oxygen, sulfur or nitrogen atom, such as ethylene oxide. The nitrogen-containing compositions of this patent are taught to be useful as additives for lubricants and fuels.

Nitro phenols have also been employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants and demulsifiers for lubricating oil and fuel compositions.

Similarly, U.S. Pat. No. 3,434,814, issued Mar. 25, 1969 to M. Dubeck et al., discloses a liquid hydrocarbon fuel composition containing a major quantity of a liquid hydrocarbon of the gasoline boiling range and a minor amount sufficient to reduce exhaust emissions and engine deposits of an aromatic nitro compound having an alkyl, aryl, aralkyl, alkanoyloxy, alkoxy, hydroxy or halogen substituent.

Mannich base condensation products of hydroxyaryl succinimides with aldehydes and amines, and derivatives thereof, are also known in the art as detergent or dispersant additives for lubricating oils and fuels.

For example, U.S. Pat. No. 4,354,950 to Hammond et al. discloses Mannich base derivatives of N-(hydroxyaryl) hydrocarbyl succinimides which are useful as detergent-dispersant additives for lubricating oils. The Mannich base derivatives described in this patent are prepared by reacting a hydrocarbyl substituted succinic anhydride with an aminophenol to produce an intermediate N-(hydroxyaryl) hydrocarbyl succinimide. This intermediate is then reacted with an alkylene diamine or polyalkylene polyamine and an aldehyde in a Mannich base reaction to produce the desired Mannich base derivatives.

U.S. Pat. No. 4,820,432 to Lundberg et al. discloses oil soluble dispersant additives useful in fuel and lubricating oil compositions which are poly ($C_5$ to $C_9$ lactone) modified Mannich base adducts made by reacting a $C_5$ to $C_9$ lactone, an amine, an aldehyde, an N-hydroxyaryl amine and a hydrocarbyl substituted $C_4$ to $C_{10}$ dicarboxylic acid producing material. The poly ($C_5$ to $C_9$ lactone) modified Mannich base adducts described in this patent may be prepared by first reacting an N-hydroxyaryl amine with a hydrocarbyl substituted $C_4$ to $C_{10}$ dicarboxylic acid producing material to form an N-hydroxyaryl hydrocarbyl substituted imide. The N-hydroxyaryl hydrocarbyl substituted imide is then reacted with an amine and an aldehyde in a Mannich base reaction to form an intermediate adduct having an amino functional group capable of initiating lactone ring opening polymerization. This intermediate adduct is subsequently reacted with a $C_5$ to $C_9$ lactone to provide the poly ($C_5$ to $C_9$ lactone) modified Mannich base adducts.

U.S. Pat. No. 5,266,081 to Avery et al. discloses multifunctional antioxidant, dispersant and detergent additives for fuels and lubricants which are Mannich base products made from an aminosalicylic acid derived hydrocarbon-substituted succinimide. The Mannich base products described in this patent are prepared by first reacting a hydrocarbon-substituted succinic anhydride with an aminosalicylic acid. The intermediate reaction product so produced is then reacted with an aldehyde and an alkylenepolyamine. The Mannich base product of this reaction is subsequently post reacted with a hydrocarbon-substituted succinic anhydride which can be the same as or different from the hydrocarbon-substituted succinic anhydride used to form the intermediate reaction product.

3

It has now been discovered that certain aryl succinimides in themselves are surprisingly useful for reducing engine deposits, especially intake valve deposits, when employed as fuel additives in fuel compositions.

SUMMARY OF THE INVENTION

The present invention provides a fuel composition comprising a major amount of hydrocarbons boiling in the gasoline or diesel range and an effective detergent amount of a compound of the formula:

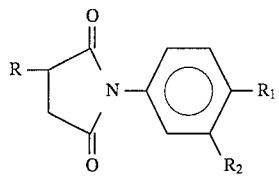

wherein R is a hydrocarbyl group having an average molecular weight of about 400 to 5,000; and $R_1$ and $R_2$ are independently selected from the group consisting of hydrogen, hydroxy, —$CO_2H$, —$NO_2$, or —$NR_3R_4$, wherein $R_3$ and $R_4$ are independently hydrogen or lower alkyl of 1 to 6 carbon atoms; provided that $R_1$ and $R_2$ cannot both be hydrogen.

The present invention additionally provides a fuel concentrate comprising an inert stable oleophilic organic solvent boiling in the range of from about 150° F. (65° C.) to 400° F. (205° C.) and from about 10 to 70 weight percent of the aryl succinimides employed in the present fuel composition.

The present invention further provides novel aryl succinimides which are useful as fuel additives for the prevention and control of engine deposits, particularly intake valve deposits.

The novel aryl succinimides of the present invention have the formula:

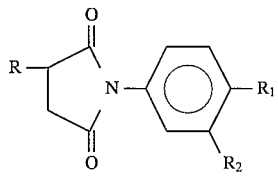

wherein R is a hydrocarbyl group having an average molecular weight of about 400 to 5,000; and $R_1$ and $R_2$ are independently selected from the group consisting of hydrogen, hydroxy, —$CO_2H$, —$NO_2$, or —$NR_3R_4$, wherein $R_3$ and $R_4$ are independently hydrogen or lower alkyl of 1 to 6 carbon atoms; provided that at least one of $R_1$ and $R_2$ is —$NO_2$ or —$NR_3R_4$.

Among other factors, the present invention is based on the discovery that certain aryl succinimides are surprisingly useful for reducing engine deposits, especially on intake valves, when employed as fuel additives in fuel compositions.

DETAILED DESCRIPTION OF THE INVENTION

The aryl succinimide fuel additives employed in the fuel composition of the present invention have the general formula:

4

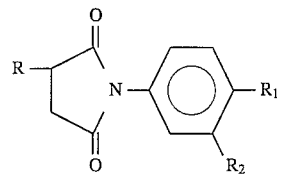

wherein R is a hydrocarbyl group having an average molecular weight of about 400 to 5,000; and $R_1$ and $R_2$ are independently selected from the group consisting of hydrogen, hydroxy, —$CO_2H$, —$NO_2$, or —$NR_3R_4$, wherein $R_3$ and $R_4$ are independently hydrogen or lower alkyl of 1 to 6 carbon atoms; provided that $R_1$ and $R_2$ cannot both be hydrogen.

Preferably, R is a hydrocarbyl group having an average molecular weight of about 500 to 3,000, more preferably about 600 to 2,000.

In addition, the hydrocarbyl group, R, is preferably an alkyl or alkenyl group, which may be straight chain or branched chain. Typically, the hydrocarbyl group is derived from an olefin or polyolefin. Preferably, R is an alkyl or alkenyl group derived from polypropylene, polybutene, or polyalphaolefin oligomers of 1-octene or 1-decene. More preferably, R is an alkyl or alkenyl group derived from polyisobutene.

Preferably, one of $R_1$ and $R_2$ is hydroxy, —$CO_2H$, —$NO_2$, or —$NR_3R_4$, and the other is hydrogen. Also preferred are those compounds wherein one of $R_1$ and $R_2$ is —$CO_2H$, —$NO_2$ or —$NR_3R_4$, and the other is hydroxy.

Preferably, $R_3$ and $R_4$ are independently hydrogen or lower alkyl of 1 to 3 carbon atoms. More preferably, $R_3$ and $R_4$ are both hydrogen; that is, —$NR_3R_4$ is amino or —$NH_2$.

For those compounds of the present invention wherein at least one of $R_1$ and $R_2$ is —$NO_2$ or —$NR_3R_4$, it is preferred that one of $R_1$ and $R_2$ is —$NO_2$ or —$NR_3R_4$, and the other is hydrogen, hydroxy or —$CO_2H$. More preferably, one of $R_1$ and $R_2$ is —$NO_2$ or —$NR_3R_4$, and the other is hydrogen or hydroxy.

The aryl succinimides employed in the present invention will generally have a sufficient molecular weight so as to be non-volatile at normal engine intake valve operating temperatures (about 200°–250° C.). Typically, the molecular weight of the aryl succinimides will range from about 600 to about 6,000, preferably from about 600 to 3,000.

Fuel soluble salts of the aryl succinimides employed in the present invention are also contemplated to be useful for preventing or controlling deposits. For those compounds containing a hydroxy group, such salts include alkali metal, alkaline earth metal, ammonium, substituted ammonium, and sulfonium salts. Preferred metal salts are the alkali metal salts, particularly the sodium and potassium salts, and the substituted ammonium salts, particularly tetraalkyl-substituted ammonium salts, such as the tetrabutylammonium salts.

Fuel-soluble salts of the aryl succinimides employed in the present invention can also be readily prepared for those compounds containing an amino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

Definitions

As used herein the following terms have the following meanings unless expressly stated to the contrary.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "amine" refers to the group, —$NH_2$.

General Synthetic Procedures

The aryl succinimide compounds employed in the present invention can be prepared by the following general methods and procedures. Those skilled in the art will recognize that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but one skilled in the art will be able to determine such conditions by routine optimization procedures.

Moreover, those skilled in the art will recognize that it may be necessary to mask or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

In the present synthetic procedures, certain amino groups on the aromatic ring may require protection and this may be accomplished by employing a standard amino protecting group, such as benzyloxycarbonyl or a trifluoroacetyl group. In addition, the aryl succinimides employed in the present invention having an amino substituent on the aromatic moiety may conveniently be prepared from the corresponding nitro derivative. Accordingly, in the following synthetic procedures, a nitro group will typically serve as a protecting group for an amino substituent.

The aryl succinimides employed in the fuel compositions of the present invention having the formula:

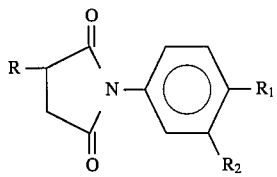
(I)

wherein R is a hydrocarbyl group having an average molecular weight of about 400 to 5,000; and $R_1$ and $R_2$ are independently selected from the group consisting of hydrogen, hydroxy, —$CO_2H$, —$NO_2$, or —$NR_3R_4$ wherein $R_3$ and $R_4$ are independently hydrogen or lower alkyl of 1 to 6 carbon atoms; provided that $R_1$ and $R_2$ cannot both be hydrogen, may be prepared by reacting a hydrocarbyl-substituted succinic anhydride of the formula:

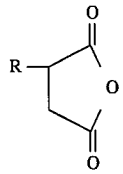
(II)

wherein R is a hydrocarbyl group having an average molecular weight of about 400 to 5,000, with an amino aromatic compound having the formula:

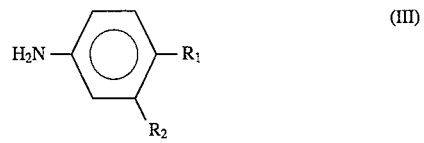
(III)

wherein $R_1$ and $R_2$ are as defined above, under conventional reaction conditions for forming succinimides. For those compounds of formula I wherein $R_1$ or $R_2$ is an amino or monoalkylamino group, the corresponding aromatic reactant of formula III will contain a suitably protected amine as the $R_1$ or $R_2$ substituent.

The hydrocarbyl-substituted succinic anhydride reactant contains a hydrocarbyl group, R, having an average molecular weight of about 400 to 5,000, preferably about 500 to 3,000, and more preferably about 600 to 2,000.

The hydrocarbyl group, R, on the hydrocarbyl-substituted succinic anhydride will preferably be an alkyl or alkenyl group, and may be straight chain or branched. Typically, the hydrocarbyl group will be derived from an olefin or polyolefin. The polyolefins employed are generally polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

A particularly preferred hydrocaryl group, R, is an alkyl or alkenyl group derived from polyisobutene.

Hydrocarbyl-substituted succinic anhydrides are well known in the art and are generally prepared by the thermal reaction of an olefin and maleic anhydride as described, for example, in U.S. Pat. Nos. 3,361,673 and 3,676,089. Alternatively, hydrocarbyl-substituted succinic anhydrides can be prepared by the reaction of chlorinated olefins with maleic anhydride, as described, for example, in U.S. Pat. No. 3,172,892.

The amino aromatic reactant is a compound of the formula:

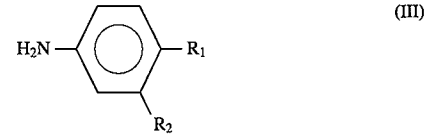
(III)

wherein $R_1$ and $R_2$ are independently selected from the group consisting of hydrogen, hydroxy, —$CO_2H$, —$NO_2$, and —$NR_3R_4$, wherein $R_3$ and $R_4$ are independently hydrogen or lower alkyl of 1 to 6 carbon atoms; provided that $R_1$ and $R_2$ cannot both be hydrogen. As noted above, when $R_1$ or $R_2$ in the final product is amino or monoalkylamino, the aromatic reactant will contain a suitably protected amine in the $R_1$ or $R_2$ position.

In the aryl succinimides derived from the aromatic reactant of formula III, preferably one of $R_1$ and $R_2$ is hydroxy, —$CO_2H$, —$NO_2$, or —$NR_3R_4$, and the other is hydrogen. Another preferred group of compounds are those wherein one of $R_1$ and $R_2$ is —$CO_2H$, —$NO_2$, or —$NR_3R_4$, and the other is hydroxy. Preferably, $R_3$ and $R_4$ are independently hydrogen or lower alkyl of 1 to 3 carbon atoms. More preferably, $R_3$ and $R_4$ are both hydrogen.

One preferred class of aryl succinimides prepared from the amino aromatic compounds of formula III are those compounds wherein at least one of $R_1$ and $R_2$ is $-NO_2$ or $-NR_3R_4$. For these compounds, preferably one of $R_1$ and $R_2$ is $-NO_2$ or $-NR_3R_4$, and the other is hydrogen, hydroxy or $-CO_2H$. More preferably, one of $R_1$ and $R_2$ is $-NO_2$ or $-NR_3R_4$, and the other is hydrogen or hydroxy. It is especially preferred that one of $R_1$ and $R_2$ is $-NO_2$ or $-NH_2$, and the other is hydrogen or hydroxy.

The amino aromatic reactants are either known compounds or can be prepared from known compounds by conventional procedures. Representative amino aromatic compounds suitable for use in the present invention, include, for example, 4-aminophenol, 4-amino-2-nitrophenol, 4-nitroaniline, 4-amino-2-hydroxybenzoic acid, 5-amino-2-hydroxybenzoic acid, 3-nitroaniline, and the like.

The reaction of the hydrocarbyl-substituted succinic anhydride with the amino aromatic compound may generally be conducted in the absence of a solvent, or alternatively, in the presence of an inert solvent, such as toluene, xylene, $C_9$ aromatic hydrocarbons, chloroform, 100 neutral oils, and the like. The reaction is typically conducted at a temperature in the range of about 80° C. to about 200° C. Reaction temperatures in the range of about 110° C. to about 170° C. are generally preferred. In general, the hydrocarbyl-substituted succinic anhydride and amino aromatic compound are reacted in equimolar amounts or with an excess of the amino aromatic compound.

When synthesizing the aryl succinimides of formula I having an amino group on the aromatic moiety (i.e., where $R_1$ or $R_2$ is an amino group), it is generally desirable to first prepare the corresponding nitro compound (i.e., where $R_1$ or $R_2$ is a nitro group), and then to reduce the nitro group to an amino group using conventional procedures. Aromatic nitro groups may be reduced to amino groups using a number of procedures that are well known in the art. For example, aromatic nitro groups may be reduced under catalytic hydrogenation conditions; or by using a reducing metal, such as zinc, tin, iron, and the like, in the presence of an acid, such as dilute hydrochloric acid.

Generally, reduction of the nitro group by catalytic hydrogenation is preferred. Typically, this reaction is conducted using about 1 to 4 atmospheres of hydrogen and a platinum or palladium catalyst, such as palladium on carbon. The reaction is typically carried out at a temperature of about 0° C. to about 100° C. for about 1 to 24 hours in an inert solvent, such as ethanol, ethyl acetate, toluene, and the like. Hydrogenation of aromatic nitro groups is discussed in further detail in, for example, P. N. Rylander, *Catalytic Hydrogenation in Organic Synthesis*, pp. 113–137, Academic Press (1979); and *Organic Synthesis, Collective Vol. I*, Second Edition., pp. 240–241, John Wiley & Sons, Inc. (1941); and references cited therein.

Fuel Compositions

The aryl succinimides employed in the present invention are useful as additives in hydrocarbon fuels to prevent and control engine deposits, particularly intake valve deposits. Typically, the desired deposit control is achieved by operating an internal combustion engine with a fuel composition containing the aryl succinimides described herein. The proper concentration of additive necessary to achieve the desired level of deposit control varies depending upon the type of fuel employed, the type of engine, and the presence of other fuel additives.

In general, the concentration of the aryl succinimides employed in this invention in hydrocarbon fuel will range from about 50 to about 2500 parts per million (ppm) by weight, preferably from 75 to 1,000 ppm. When other deposit control additives are present, a lesser amount of the present additive may be used.

The aryl succinimides employed the present invention may also be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the aryl succinimides employed in this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, synthetic polyoxyalkylene-derived oils, such as those described, for example, in U.S. Pat. No. 4,191,537 to Lewis and U.S. Pat. No. 4,877,416 to Campbell, and polyesters, such as those described, for example, in U.S. Pat. Nos. 3,756,793 and 5,004,478 to Robinson and Vogel et al., respectively, and in European Patent Application Nos. 356,726 and 382,159, published Mar. 7, 1990 and Aug. 16, 1990, respectively.

These carrier fluids are believed to act as a carrier for the fuel additives of the present invention and to assist in removing and retarding deposits. The carrier fluid may also exhibit synergistic deposit control properties when used in combination with an aryl succinimide additive employed in this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

EXAMPLES

The following examples are presented to illustrate specific embodiments of the present invention and synthetic preparations thereof; and therefore these examples should not be interpreted as limitations upon the scope of this invention.

Example 1

To a flask equipped with a magnetic stirrer, Dean-Stark trap, thermometer, reflux condensor and nitrogen inlet was added 50.0 grams of polyisobutenylsuccinic anhydride (0.042 moles, saponification number=95.1) where the polyisobutenyl group has an approximate molecular weight of 950 and 6.9 grams of 4-aminophenol. The mixture was heated to 160° for sixteen hours, then cooled to room temperature and diluted with 1.5 L of hexane. The organic phase was washed twice with 1% aqueous hydrochloric acid, once with water and once with saturated aqueous sodium chloride. The organic layer was dried over anhydrous magnesium sulfate, filtered and the solvents removed in vacuo to yield 53.1 grams of product as a brown oil. The oil was chromatographed on silica gel eluting with hexane, followed by hexane/ethyl acetate/ethanol (70:28:2) to yield 31.0 grams of the desired succinimide as a brown oil.

Example 2

To a flask equipped with a magnetic stirrer, Dean-Stark trap, thermometer, reflux condensor and nitrogen inlet was added 50.0 grams of polyisobutenylsuccinic anhydride (0.040 moles, saponification number=90.6) where the polyisobutenyl group has an approximate molecular weight of 950 and 9.3 grams of 4-amino-2-nitrophenol. The mixture was heated to 160° C. for sixteen hours, then cooled to room temperature and diluted with 1.5 L of hexane. The organic phase was washed twice with 1% aqueous hydrochloric acid, once with water and once with saturated aqueous sodium chloride. The organic layer was dried over anhydrous magnesium sulfate, filtered and the solvents removed in vacuo to yield 51.0 grams of product as a brown oil. The oil was chromatographed on silica gel eluting with hexane, followed by hexane/ethyl acetate/ethanol (90:8:2) to yield 21.0 grams of the desired succinimide as a brown oil.

Example 3

A solution of 6.0 grams of the product from Example 2 in 200 mL of ethyl acetate containing 1.0 gram of 10% palladium on charcoal was hydrogenated at 35–40 psi for 16 hours on a Parr low-pressure hydrogenator. Catalyst filtration and removal of the solvent in vacuo yielded 4.5 grams of the desired amino aromatic succinimide as a brown oil.

Example 4

To a flask equipped with a magnetic stirrer, Dean-Stark trap, thermometer, reflux condensor and nitrogen inlet was added 40.0 grams of polyisobutenylsuccinic anhydride (0.032 moles, saponification number=90.6) where the polyisobutenyl group has an approximate molecular weight of 950 and 6.7 grams of 4-nitroaniline. The mixture was heated to 160° C. for sixteen hours, then cooled to room temperature and diluted with 1.5 L of hexane. The organic phase was washed twice with 1% aqueous hydrochloric acid, once with water and once with saturated aqueous sodium chloride. The organic layer was dried over anhydrous magnesium sulfate, filtered and the solvents removed in vacuo to yield a brown oil. The oil was chromatographed on silica gel eluting with hexane, followed by hexane/ethyl acetate/ethanol (90:8:2) to yield 21.7 grams of the desired succinimide as a brown oil.

Example 5

A solution of 16.7 grams of the product from Example 4 in 200 mL of ethyl acetate containing 2.0 grams of 10% palladium on charcoal was hydrogenated at 35–40 psi for 16 hours on a Parr low-pressure hydrogenator. Catalyst filtration and removal of the solvent in vacuo yielded 15.7 grams of the desired amino aromatic succinimide as a yellow oil.

Example 6

To a flask equipped with a magnetic stirrer, Dean-Stark trap, thermometer, reflux condensor and nitrogen inlet was added 50.0 grams of polyisobutenylsuccinic anhydride (0.040 moles, saponification number=90.6) where the polyisobutenyl group has an approximate molecular weight of 950 and 9.3 grams of 4-amino-2-hydroxybenzoic acid. The mixture was heated to 160° C. for sixteen hours, then cooled to room temperature. The oil was chromatographed on silica gel eluting with hexane, followed by hexane/ethyl acetate/ethanol (80:18:2) to yield 26.6 grams of the desired succinimide as a brown oil.

Example 7

To a flask equipped with a magnetic stirrer, Dean-Stark trap, thermometer, reflux condensor and nitrogen inlet was added 50.0 grams of polyisobutenylsuccinic anhydride (0.040 moles, saponification number=90.6) where the polyisobutenyl group has an approximate molecular weight of 950 and 9.3 grams of 5-amino-2-hydroxybenzoic acid. The mixture was heated to 160° C. for sixteen hours, then cooled to room temperature. The oil was chromatographed on silica gel eluting with hexane, followed by hexane/ethyl acetate/ethanol (90:8:2) to yield 17.0 grams of the desired succinimide as a brown oil.

Example 8

To a flask equipped with a magnetic stirrer, Dean-Stark trap, thermometer, reflux condensor and nitrogen inlet was added 40.0 grams of polyisobutenylsuccinic anhydride (0.032 moles, saponification number=90.6) where the polyisobutenyl group has an approximate molecular weight of 950 and 6.7 grams of 3-nitroaniline. The mixture was heated to 160° C. for sixteen hours, then cooled to room temperature and diluted with 1.5 L of hexane. The organic phase was washed twice with 1% aqueous hydrochloric acid, once with water and once with saturated aqueous sodium chloride. The organic layer was dried over anhydrous magnesium sulfate, filtered and the solvents removed in vacuo to yield a brown oil. The oil was chromatographed on silica gel eluting with hexane, followed by hexane/ethyl acetate/ethanol (90:8:2) to yield 13.5 grams of the desired succinimide as a brown oil.

Example 9

A solution of 8.7 grams of the product from Example 8 in 200 mL of ethyl acetate containing 2.0 grams of 10% palladium on charcoal was hydrogenated at 35–40 psi for 16 hours on a Parr low-pressure hydrogenator. Catalyst filtration and removal of the solvent in vacuo yielded 7.2 grams of the desired amino aromatic succinimide as a yellow oil.

Example 10

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30 W oil.

The amount of carbonaceous deposit in milligrams on the intake valves is reported for each of the test compounds in Table I.

TABLE I

| Sample[1] | Intake Valve Deposit Weight (in milligrams) | | |
|---|---|---|---|
| | Run 1 | Run 2 | Average |
| Base Fuel | 253.4 | 235.5 | 244.5 |
| Example 1 | 32.0 | 69.0 | 50.5 |
| Example 2 | 82.3 | 88.5 | 85.4 |
| Example 3 | 17.7 | 8.1 | 12.9 |
| Example 4 | 128.3 | 98.6 | 113.5 |
| Example 5 | 21.9 | 18.0 | 20.0 |
| Example 6 | 54.0 | — | 54.0 |
| Example 7 | 60.5 | 70.4 | 65.5 |
| Example 8 | 108.4 | 126.8 | 117.6 |
| Example 9 | 25.8 | 8.2 | 17.0 |

[1]At 150 parts per million actives (ppma).

The base fuel employed in the above single-cylinder engine tests was a regular octane unleaded gasoline containing no fuel detergent. The test compounds were admixed with the base fuel to give a concentration of 150 ppma (parts per million actives).

The data in Table I illustrates the significant reduction in intake valve deposits provided by the aryl succinimides employed in the present invention (Examples 1 to 9) compared to the base fuel.

What is claimed is:

1. A fuel composition comprising a major amount of hydrocarbons boiling in the gasoline or diesel range and an effective detergent amount of a compound of the formula:

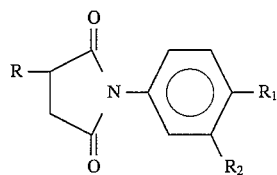

wherein R is a hydrocarbyl group having an average molecular weight of about 600 to 2,000; and $R_1$ and $R_2$ are independently selected from the group consisting of hydrogen, hydroxy, —$CO_2H$, —$NO_2$, and —$NR_3R_4$, wherein $R_3$ and $R_4$ are independently hydrogen or lower alkyl of 1 to 6 carbon atoms; provided that $R_1$ and $R_2$ cannot both be hydrogen and further provided that when one of $R_1$ and $R_2$ is —$NR_3R_4$ or $CO_2H$, the other may not be hydrogen.

2. The fuel composition according to claim 1, wherein R is an alkyl or alkenyl group.

3. The fuel composition according to claim 2, wherein R is an alkyl or alkenyl group derived from polypropylene, polybutene, or polyalphaolefin oligomers of 1-octene or 1-decene.

4. The fuel composition according to claim 3, wherein R is an alkyl or alkenyl group derived from polyisobutene.

5. The fuel composition according to claim 1, wherein one of $R_1$ and $R_2$ is hydroxy, or —$NO_2$, and the other is hydrogen.

6. The fuel composition according to claim 5, wherein one of $R_1$ and $R_2$ is —$NO_2$, and the other is hydrogen.

7. The fuel composition according to claim 1, wherein one of $R_1$ and $R_2$ is —$CO_2H$, —$NO_2$ or —$NR_3R_4$, and the other is hydroxy.

8. The fuel composition according to claim 7, wherein one of $R_1$ and $R_2$ is —$NO_2$ or —$NR_3R_4$, and the other is hydroxy.

9. The fuel composition according to claim 8, wherein one of $R_1$ and $R_2$ is —$NO_2$ or —$NH_2$, and the other is hydroxy.

10. A fuel concentrate comprising an inert stable oleophilic organic solvent boiling in the range of from about 150° F. to 400° F. and from about 10 to about 70 wt % of a compound of the formula:

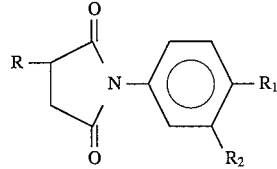

wherein R is a hydrocarbyl group having an average molecular weight of about 600 to 2,000; and $R_1$ and $R_2$ are independently selected from the group consisting of hydrogen, hydroxy, —$CO_2H$, —$NO_2$, and —$NR_3R_4$, wherein $R_3$ and $R_4$ are independently hydrogen or lower alkyl of 1 to 6 carbon atoms; provided that $R_1$ and $R_2$ cannot both be hydrogen and further provided that when one of $R_1$, and $R_2$ is —$NR_3R_4$ or $CO_2H$, the other may not be hydrogen.

11. The fuel concentrate according to claim 10, wherein R is an alkyl or alkenyl group.

12. The fuel concentrate according to claim 11, wherein R is an alkyl or alkenyl group derived from polypropylene, polybutene, or polyalphaolefin oligomers of 1-octene or 1-decene.

13. The fuel concentrate according to claim 12, wherein R is an alkyl or alkenyl group derived from polyisobutene.

14. The fuel concentrate according to claim 10, wherein one of $R_1$ and $R_2$ is hydroxy, or —$NO_2$, and the other is hydrogen.

15. The fuel concentrate according to claim 14, wherein one of $R_1$ and $R_2$ is —$NO_2$, and the other is hydrogen.

16. The fuel concentrate according to claim 10, wherein one of $R_1$ and $R_2$ is —$CO_2H$, —$NO_2$ or —$NR_3R_4$, and the other is hydroxy.

17. The fuel concentrate according to claim 16, wherein one of $R_1$ and $R_2$ is —$NO_2$ or —$NR_3R_4$, and the other is hydroxy.

18. The fuel concentrate according to claim 17, wherein one of $R_1$ and $R_2$ is —$NO_2$ or —$NH_2$, and the other is hydroxy.

19. A compound of the formula:

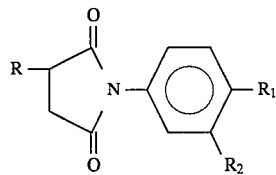

wherein R is a hydrocarbyl group having an average molecular weight of about 400 to 5,000; and $R_1$ and $R_2$ are independently selected from the group consisting of hydroxy, —$CO_2H$, —$NO_2$, and —$NR_3R_4$, wherein $R_3$ and $R_4$ are independently hydrogen or lower alkyl of 1 to 6 carbon atoms; provided that at least one of $R_1$ and $R_2$ is —$NO_2$ or —$NR_3R_4$.

20. The compound according to claim 19, wherein R has an average molecular weight of about 500 to 3,000.

21. The compound according to claim 20, wherein R has an average molecular weight of about 600 to 2,000.

22. The compound according to claim 19, wherein R is an alkyl or alkenyl group.

23. The compound according to claim 22, wherein R is an alkyl or alkenyl group derived from polypropylene, polybutene, or polyalphaolefin oligomers of 1-octene or 1-decene.

24. The compound according to claim 23, wherein R is an alkyl or alkenyl group derived from polyisobutene.

25. The compound according to claim 19, wherein one of $R_1$ and $R_2$ is —$NO_2$ or —$NR_3R_4$, and the other is hydroxy or —$CO_2H$.

26. The compound according to claim 25, wherein one of $R_1$ and $R_2$ is —$NO_2$ or —$NR_3R_4$, and the other is hydroxy.

27. The compound according to claim 26, wherein one of $R_1$ and $R_2$ is —$NO_2$ or —$NH_2$, and the other is hydroxy.

* * * * *